(12) United States Patent
DeSilva et al.

(10) Patent No.: US 7,387,037 B2
(45) Date of Patent: Jun. 17, 2008

(54) DISPENSING APPARATUS

(75) Inventors: Brett L. DeSilva, Torrance, CA (US); Richard A. Carl, Rancho Pales Verdes, CA (US); Daniel D. Dechert, Torrance, CA (US)

(73) Assignee: PerkinElmer Las, Inc., Boston, MA (US)

( * ) Notice: Subject to any disclaimer, the term of this patent is extended or adjusted under 35 U.S.C. 154(b) by 527 days.

(21) Appl. No.: 11/171,687

(22) Filed: Jun. 30, 2005

(65) Prior Publication Data

US 2005/0245113 A1    Nov. 3, 2005

Related U.S. Application Data

(63) Continuation of application No. 10/214,943, filed on Aug. 7, 2002.

(51) Int. Cl.
*G01N 1/00*    (2006.01)
(52) U.S. Cl. .................................................. 73/863.31
(58) Field of Classification Search ...................... None
See application file for complete search history.

(56) References Cited

U.S. PATENT DOCUMENTS

| | | | |
|---|---|---|---|
| 5,497,670 A | 3/1996 | Carl | 73/863.32 |
| 5,736,105 A | 4/1998 | Astle | 422/100 |
| 6,024,925 A | 2/2000 | Little et al. | 422/100 |
| 6,101,946 A | 8/2000 | Martinsky | 101/494 |
| 6,116,099 A | 9/2000 | Carl | 73/864.14 |
| 6,269,846 B1 | 8/2001 | Overbeck et al. | 141/1 |
| 6,447,723 B1 | 9/2002 | Schermer et al. | 422/62 |
| 6,551,557 B1 | 4/2003 | Rose et al. | 422/100 |
| 2001/0049149 A1 | 12/2001 | Kennedy et al. | 436/180 |
| 2002/0053245 A1 | 5/2002 | Carl | 73/864.14 |
| 2002/0072068 A1 | 6/2002 | Nakao et al. | 435/6 |

*Primary Examiner*—Robert R Raevis
(74) *Attorney, Agent, or Firm*—Seed IP Law Group PLLC (57) ABSTRACT

A pin support assembly includes a pin support frame having a plurality of apertures for supporting an array of pins for dispensing fluids. The pins are supported for longitudinal or "floating" movement to prevent damage to the pins. An actuation assembly engages an end of each of the pins to ensure that the pins are properly seated in the support frame in a planar fashion. The actuation assembly engages the pins as the pins move relatively toward a head block and disengages the pins as the pins move relatively away from the head block.

20 Claims, 7 Drawing Sheets

Fig. 12

DISPENSING APPARATUS

CROSS-REFERENCE TO RELATED APPLICATION

This application is a continuation of U.S. patent application Ser. No. 10/214,943, filed Aug. 7, 2002, now pending.

BACKGROUND OF THE INVENTION

1. Field of the Invention

The present invention is generally related to apparatus for dispensing controlled amounts of fluid.

2. Description of the Related Art

Many research and/or manufacturing settings require the delivery of a precise amount of fluid. Precisely controlling the delivery of fluid can be important to producing accurate test results or to producing high quality products, as well as being important in lowering costs associated with such operations. Often, these applications require a large number of repetitive operations. For example, biological or chemical assays may employ hundreds, thousands, or more of individual testing steps. Efficiency, accuracy and repeatability require that these operations be automated. One method of automating is to perform multiple tests at discrete locations on a single plate (i.e., plate, slide, or array). This requires the delivery of very precise amounts of fluids, for example agents or reagents, to hundreds or even thousands of locations on the plate. Other automated methods are of course possible. The cost of high precision automated equipment is typically substantial.

One approach to delivery of a controlled amount of fluid employs pipette tips. The pipette tip relies on capillary action to draw a precise amount of fluid from a reservoir into an internal passage of the pipette tip, for delivery to the desired location. Pipette tips may be particularly suitable for dispensing fluids in the micro-liter range.

U.S. Pat. No. 5,497,670 issued Mar. 12, 1996 discloses a dispensing apparatus including means for loading pipette tips carried by a pipette plate onto dispensing cylinders such that a loading force is maintained during the operation to ensure a hermetic seal. The pipette tips are manually placed on the pipette tip plate, the pipette tip plate being slidingly received within the dispensing apparatus.

U.S. patent application Ser. No. 08/751,859 filed Nov. 18, 1996 discloses a dispensing apparatus. The dispensing apparatus is similar to that disclosed in the aforementioned patent, but substitutes a more conventional pipette tip carrier for the pipette tip plate, which is less expensive, less likely to be contaminated, and easily adapted for robotic operation or automation.

U.S. application Ser. No. 10/027,448 filed Dec. 20, 2001 discloses a dispensing apparatus that employs a modified pipette tip box tray carrier to furnish pipette tips carried in a standard pipette tip box to the apparatus, and includes engagement means to engage pipette tip box tray carrier such that the pipette tips are loaded into corresponding internal cylinders formed in a dispense block head of the dispensing apparatus. The dispense block head comprises a solid block of material having a plurality of internal cylinders to engage the pipette tips in a sealing engagement.

A distinctly different approach to precisely dispensing fluids employs one or more pins to retrieve a desired amount of fluid from a reservoir, and to dispense the retrieved fluid to a desired location. In contrast to pipette tips, these pins do not include an internal passage, but rather retrieve a small sample of the fluid as the pin is removed from a reservoir, the fluid forming a droplet on the outer surface at the end of the pin. The amount of fluid retrieved by the pin is a function of a number of parameters including the size, shape and material of the pin and the viscosity of the fluid, all of which affect surface tension. The pin based approach may be particularly suitable for dispensing fluids in the nano-liter range.

Automating the pin based approach would be highly desirable, as would be the taking advantage of the substantial investment made in existing automated equipment such as pipette based dispensing apparatus.

BRIEF SUMMARY OF THE INVENTION

In one aspect, a pin support assembly includes a pin support frame having a plurality of apertures for supporting an array of pins for dispensing fluids. An actuation assembly engages an end of each of the pins to ensure that the pins are properly seated in the support frame in a planar fashion. Interchangeability of the pin support frame with a pipette box tray carrier allows a single drive mechanism to be employed for different operations, for example dispensing very small amounts of fluid versus dispensing very large amounts of fluid, reducing costs.

In another aspect, a pin support assembly for use with a dispense head apparatus having a movable piston plate includes a pin engagement actuation member selectively positionable with respect to the dispense head apparatus to be moved by the piston plate of the dispense head apparatus, a pin engagement member opposed to the pin engagement actuation member and mounted for movement with respect thereto, a biasing member coupled to bias the pin engagement member and the first pin engagement actuation member away from one another, and a linkage coupling the pin engagement actuation member and the pin engagement member to selectively move the pin engagement member and the first pin engagement actuation member towards one another. The pins are supported for longitudinal or "floating" movement to prevent damage to the pins.

In another aspect, a pin support assembly for supporting pins for use with a dispense head apparatus having a movable piston plate and a carrier plate includes a first pin support surface having a first plurality of apertures of a first diameter, a second pin support surface having a second plurality of apertures of a second diameter, the second diameter smaller than the first diameter, the second pin support surface spaced from and coupled to the first pin support surface to form a pin support frame, a pin engagement member opposed to the first pin support surface and mounted for movement with respect thereto between an engaged position where the pin engagement member contacts a respective end of each of a number of pins received in the first and the second apertures of the first and the second pin support surfaces of the pin support frame, if any, and an unengaged position spaced from the engaged position to disengage the respective ends of the pins received in the first and the second apertures of the first and the second pin support surfaces of the pin support frame, if any; a movable pin engagement actuation member opposed to and spaced across the pin engagement member from the pin support frame, a scissors linkage coupling the pin engagement actuation member and the pin engagement member to selectively move the pin engagement member and the first pin engagement actuation member towards and away from one another, a biasing member coupled to bias the pin engagement member toward the disengaged position, and a set of mounting members sized to receive a set of loading pins on the carrier plate of the dispense head apparatus to selectively position the pin support assembly with respect to the dispense head apparatus such that the pin engagement actuation member is movable by the piston plate of the dispense head apparatus.

In yet another aspect, a dispensing apparatus includes a pin support frame having a plurality of pin receiving apertures, a pin engagement member having a substantially planar pin engagement surface, the pin engagement member selectively movable between an engaged position and a disengaged position spaced from the engaged position, the pin engagement surface being proximate the pin support frame when the pin engagement member is in the engaged position and the pin engagement surface being distal to the pin support frame when pin engagement member is in the disengaged position, a pin engagement actuation member spaced across the pin engagement member from the pin support frame and movable between a first position spaced relatively from the pin support frame and a second position spaced relatively toward the pin support frame, a linkage coupling the pin engagement actuation member and the pin engagement member to selectively move the pin engagement member towards the pin engagement actuation member as the pin engagement member moves toward the disengaged position and to move the pin engagement member away from the pin engagement actuation member as the pin engagement member moves towards the engaged position, and a drive member couplable to selectively move the pin engagement actuation member between the first position and the second position.

In yet a further aspect, a dispensing apparatus includes a pin support frame having a first plurality of pin receiving apertures of a first diameter and a second plurality of pin receiving apertures of a second diameter smaller than the first diameter, each of the pin receiving apertures of the first plurality aligned with a respective one of the pin receiving apertures of the second plurality for supportingly receiving a respective pin for axial movement with respect thereto, and a pin engagement member having a substantially planar pin engagement surface, the pin engagement member selectively positionable between an engaged position to contact the pins received in the pin receiving apertures if any, and a disengaged position spaced from the engaged position.

In yet a further aspect a dispensing apparatus includes a drive assembly including a drive assembly frame, a drive member mounted to the drive assembly frame for axial movement with respect thereto, and a pin support assembly including a pin support frame having a number of apertures for slidingly receiving a plurality of pins, a pin engagement member mounted for movement with respect to the pin support frame between an engaged position and a disengaged position, and a linkage coupled to move the pin engagement member toward the disengaged position when the drive member moves towards the pin support frame and to move the pin engagement member toward the engaged position when the drive member moves away from the pin support frame, wherein the pin support assembly is selectively attachable and detachable to the drive assembly.

In yet an even further aspect, a dispensing apparatus includes pin support means for supporting each of a plurality of pins, a pin engagement member selectively positionable between an engaged position simultaneously engaging in a single plane a respective end of each of a plurality of pins and a disengaged position spaced from the engaged position, and actuating means for moving the pin engagement member between the engaged and the disengaged positions.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrary enlarged and positioned to improve drawing legibility. Further, the particular shapes of the elements, as drawn are not intended to convey any information regarding an actual shape of the particular elements, and are solely selected for ease of recognition in the drawings.

DETAILED DESCRIPTION OF THE INVENTION

In the following description, certain specific details are set forth in order to provide a thorough understanding of various embodiments of the invention. However, one skilled in the art will understand that the invention may be practiced without these details. In other instances, well-known structures associated with dispensing apparatus, actuators, motors, motor controllers, and automated systems and devices have not been shown or described in detail to avoid unnecessarily obscuring descriptions of the embodiments of the invention.

Unless the context requires otherwise, throughout the specification and claims which follow, the word "comprise"

and variations thereof, such as "comprises" and "comprising" are to be construed in an open, inclusive sense, that is as "including, but not limited to."

The headings provided herein are for convenience only and do not interpret the scope or meaning of the claimed invention.

Figure 1:
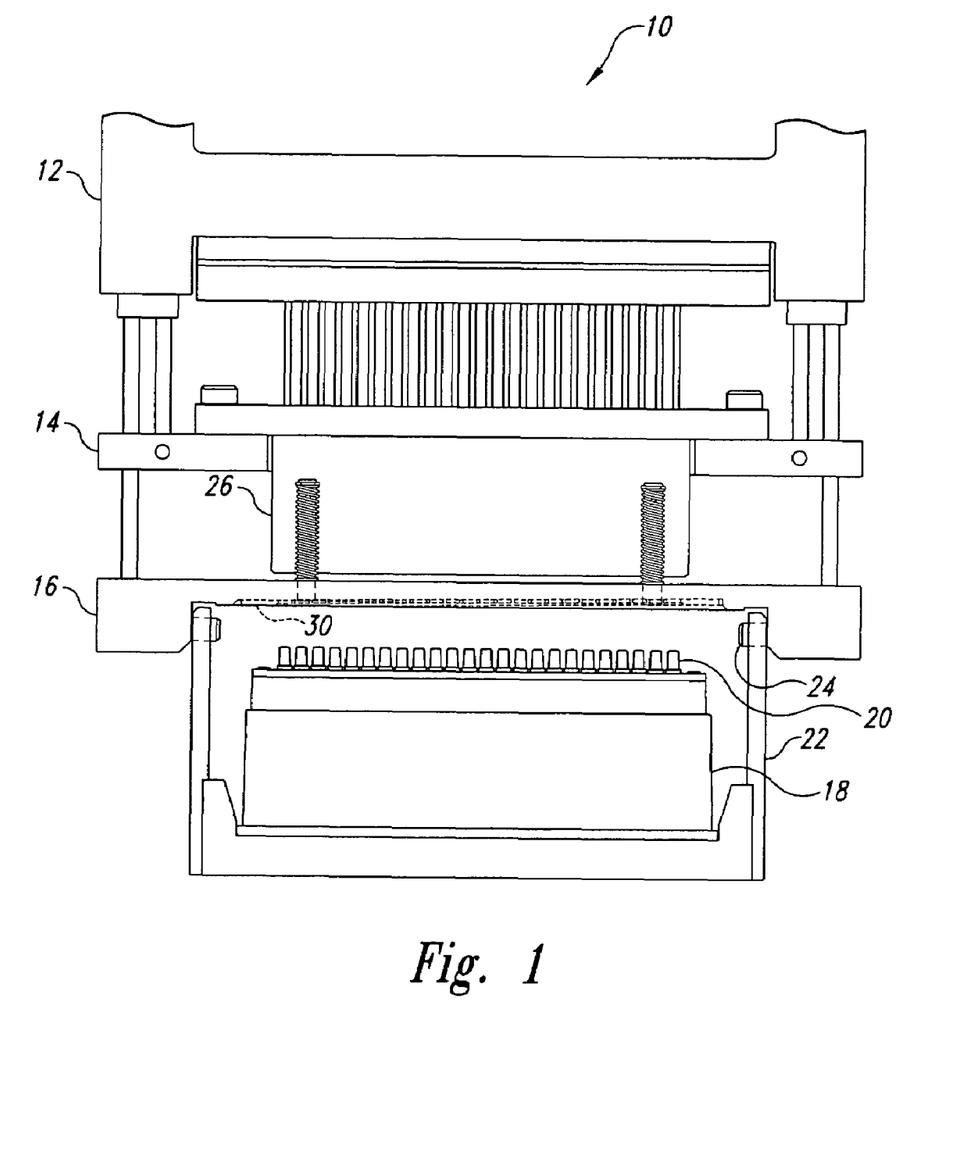
FIG. 1 is a front elevational view of a fluid dispensing apparatus with a pipette tip box tray carrier in a disengaged position to load a pipette tip box holding a plurality of pipette tips.
Figures 2, 10:
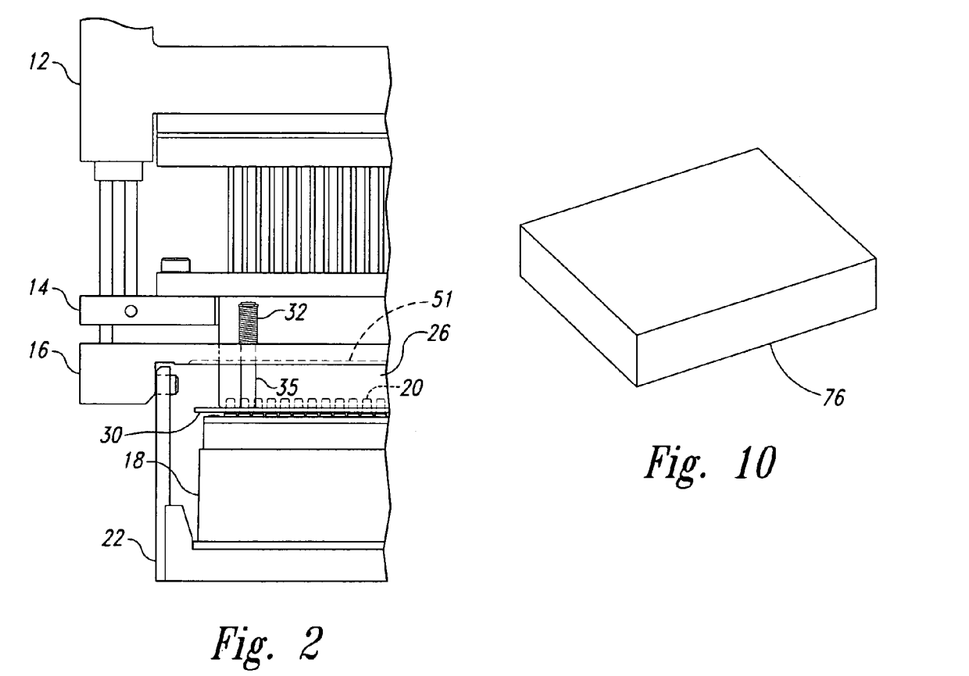
FIG. 2 is a partial front elevational view of the fluid dispensing apparatus of FIG. 1 with the pipette tip box tray carrier in an engaged position to engage the pipette tips in the pipette tip box with respective ones of internal cylinders formed in a dispense block head of the fluid dispensing apparatus.
FIG. 10 is an top, front, right isometric view of an alternative block of the fluid dispensing apparatus of FIG. 1.

FIGS. 1 and 2 show a fluid dispensing apparatus 10 that includes a piston plate 12, a horseshoe plate 14, and a carrier plate 16. The fluid dispensing apparatus 10 may employ a pipette tip box 18 that holds a number of pipette tips 20 for retrieving and dispensing defined amounts of fluids. The pipette tip box 18 is detachably coupled to the carrier plate 16 by way of a pipette box tray carrier 22. In the illustrated example, the pipette box tray carrier 22 includes a pair of L-shaped ears or lugs for engaging and disengaging a set of loading pins 24 of the moveable carrier plate 16.

In operation, a pipette tip box 18 loaded with a plurality of pipette tips 20 is loaded onto the pipette box tray carrier 22. The pipette box tray carrier 22 is coupled to the carrier plate 16. The pipette box tray carrier 22 moves relative to a dispense block head 26 to selectively engage the ends of the pipette tips 20 with respective ones of a number of internal cylinders formed in the dispense block head 26. The structure and operation of the fluid dispensing apparatus 10 of FIGS. 1 and 2 is further described in U.S. patent application Ser. No. 08/751,859, filed Nov. 18, 1996, and in U.S. patent application Ser. No. 09/442,500, filed Dec. 20, 2001, and thus will not be repeated herein in the interest of brevity and clarity.

Figure 3:
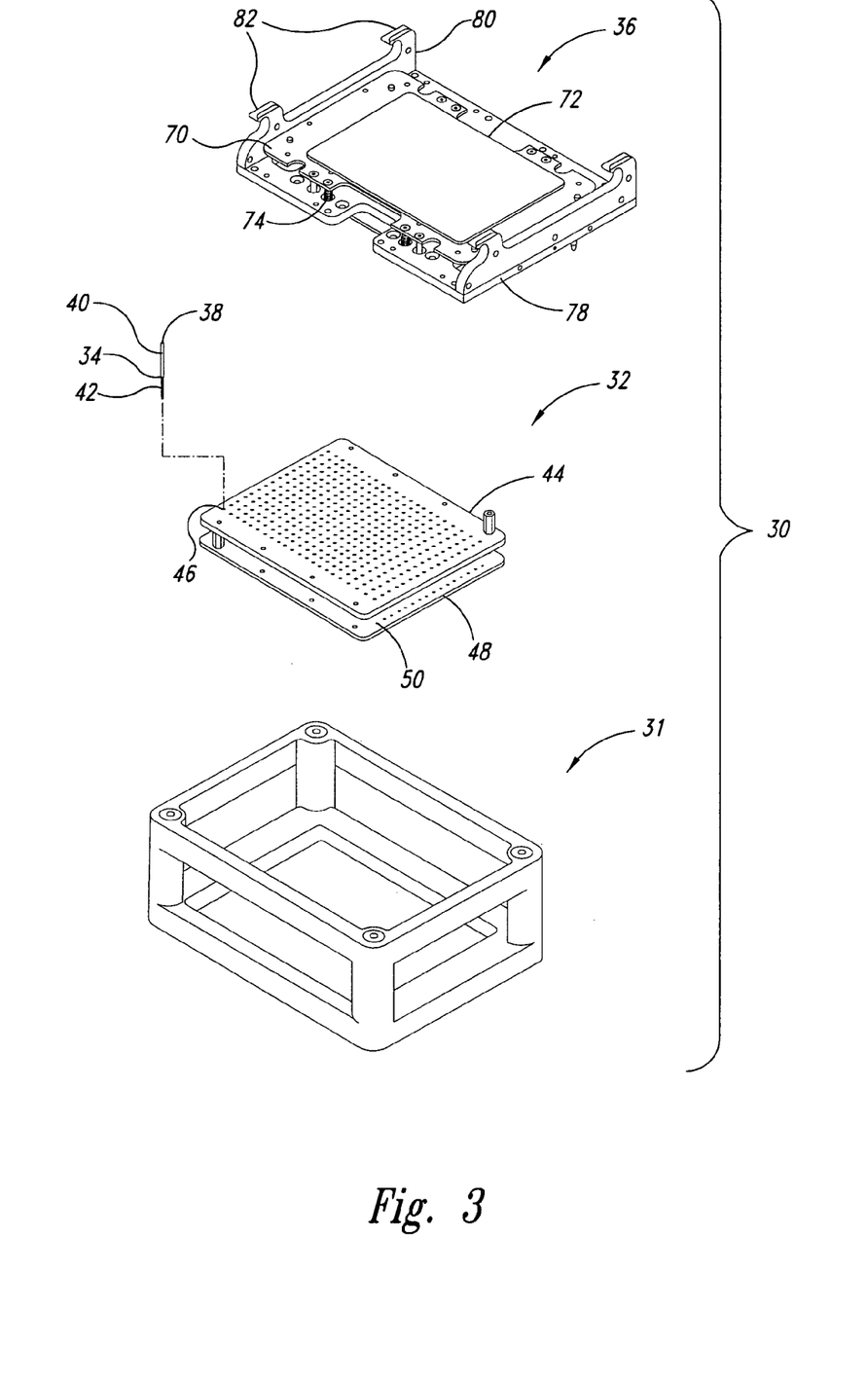
FIG. 3 is a partially exploded top, front, right isometric view of a pin support assembly having a pin support frame and an actuation assembly for use with the fluid dispensing apparatus of FIGS. 1 and 2, for example, as a substitute for the pipette tip box and pipette tip box tray carrier thereof.
Figure 4:
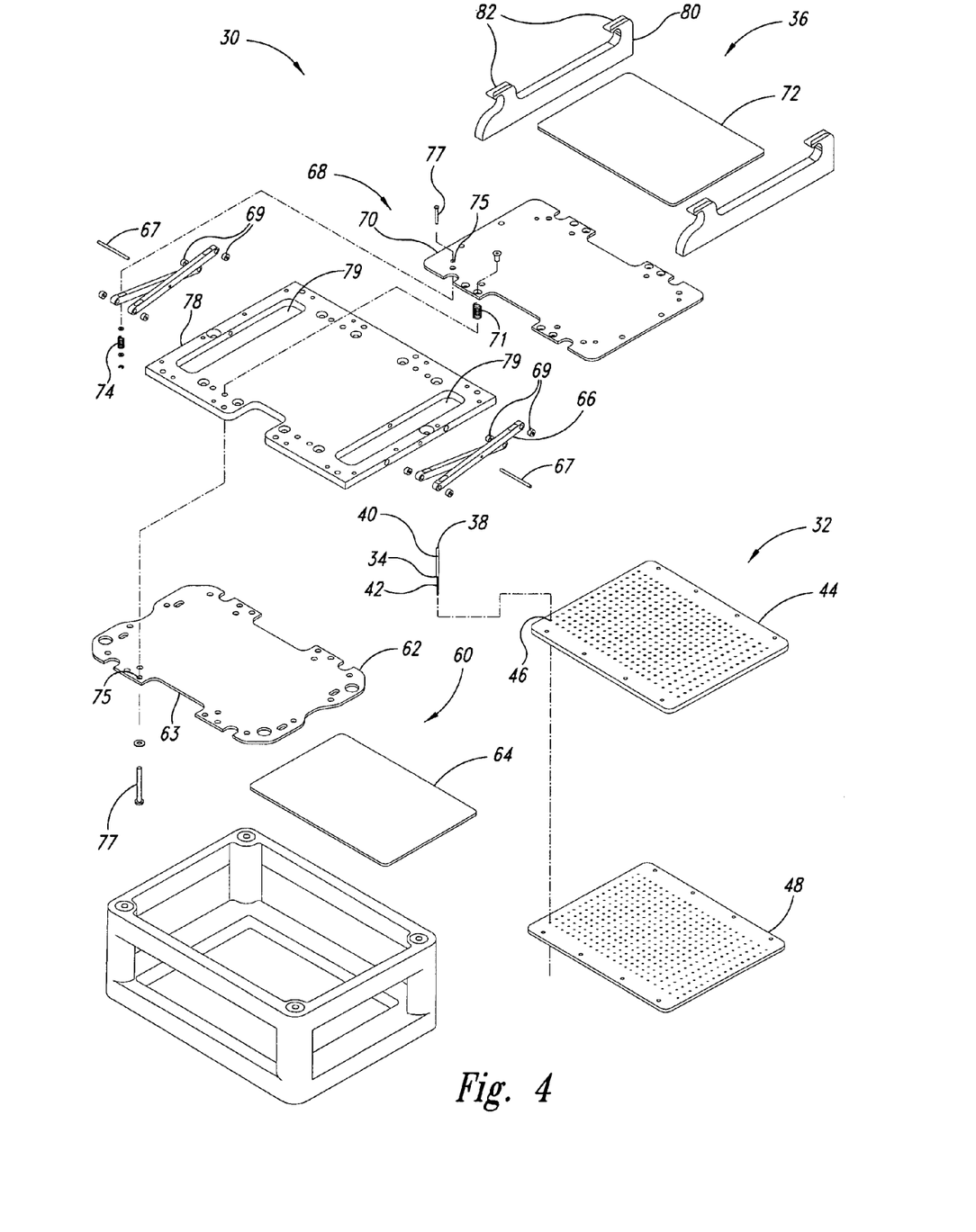
FIG. 4 is a further exploded top, front, right isometric view of a pin support assembly of FIG. 3.

FIGS. 3 and 4 show a pin support assembly 30 for use with dispensing apparatus, such as the dispensing apparatus 10 of FIG. 1. The pin support assembly 30 includes a frame 31, a pin support frame 32 for supporting a plurality of pins 34 and an actuation assembly 36 for selectively engaging ends 38 of the pins 34. The frame 31 may support the pin support frame 32 and protect the pins 34 from damage.

Each of the pins 34 has a first portion 40 of a first diameter and a second portion 42 of a second diameter less than the first diameter. The amount of fluid drawn by the pin 34 will in part be a function of the second diameter. In the embodiment illustrated in FIGS. 3 and 4, the pin support frame 32 includes a first frame member 44 having a plurality of apertures 46 having diameters slightly greater than the first diameter of the first portion 40 of the pin 34. The pin support frame 32 also includes a second frame member 48 having a plurality of apertures 50 having diameters slightly greater than the second diameter of the second portion 42 of the pin 34. The apertures 50 of the second frame member 48 are aligned or in registration with a respective one of the apertures 46 of the first frame member 44. Each of the pins 34 is received in a respective pair of the apertures 46, 50 for axial movement with respect thereto. The second support frame 48 serves as a stop, engaging an edge formed between the first and second portions 40, 42 of the pins 34 to limit the axial travel of the pins 34.

Figure 5:
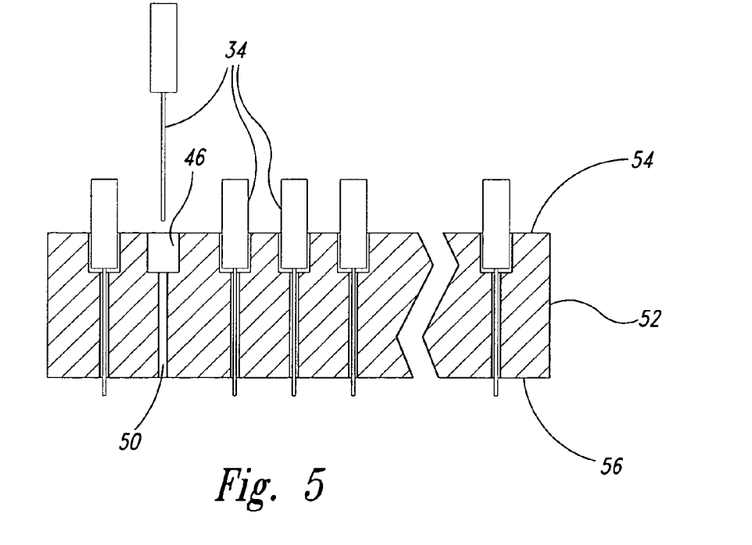
FIG. 5 is a view of an alternative embodiment of the pin support frame of the pin support frame of FIGS. 3 and 4.

FIG. 5 shows an alternative embodiment of the pin support frame 32 employing a single frame member 52 having apertures 46 formed in an upper surface 54 and apertures 50 formed in a lower surface 56. The pins 34 are again supported for axial movement, the difference in the diameters of the first aperture 46 and the second aperture 50 forming a stop to limit the axial travel of the pins 34.

Figure 6:
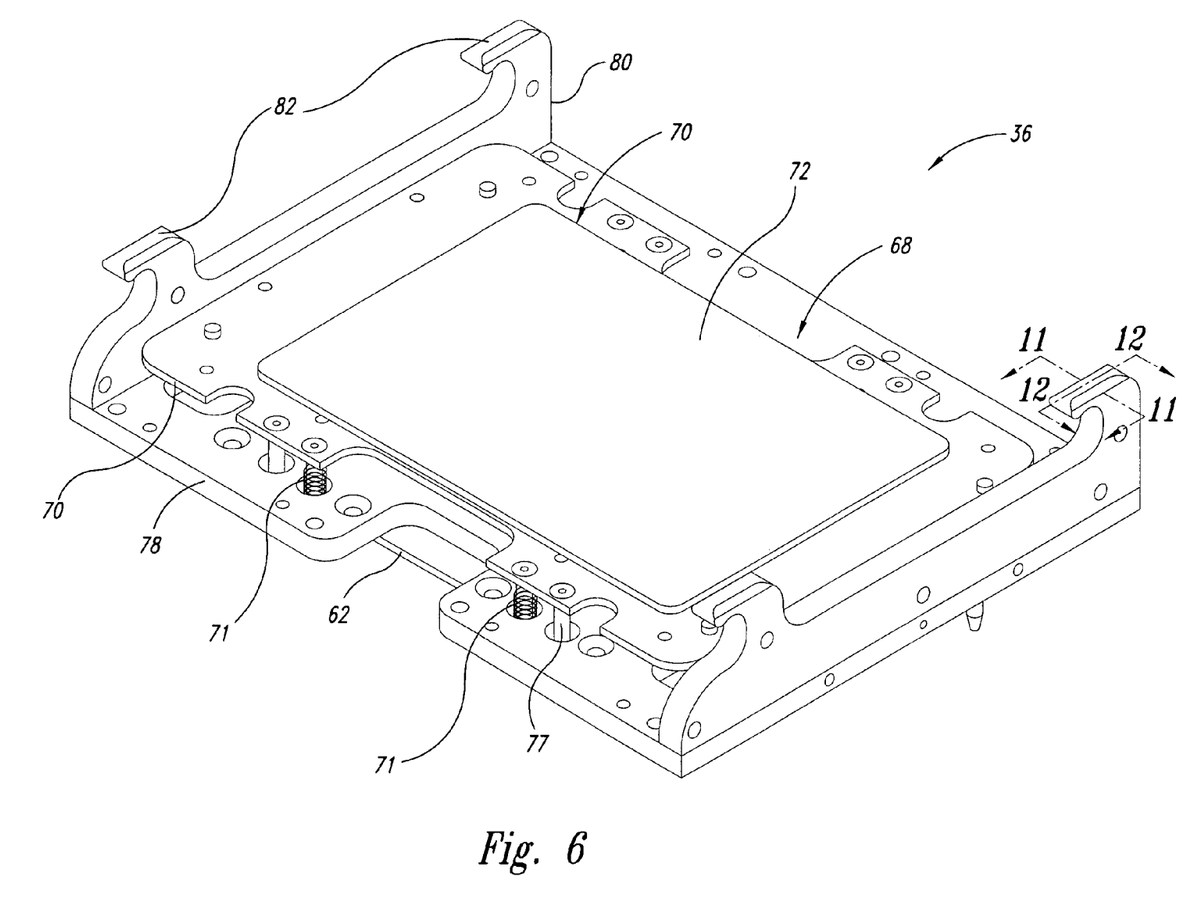
FIG. 6 is a top, front, right isometric view of the actuation assembly of the pin support assembly of FIG. 3.
Figure 7:
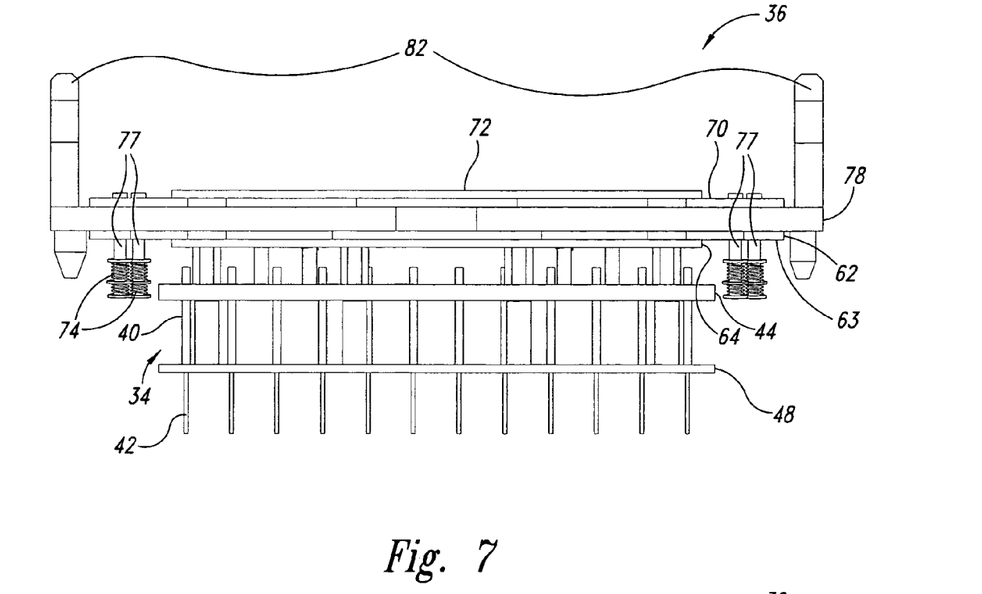
FIG. 7 is a front elevational view of the actuation assembly of FIG. 6 in a pin engaged position.
Figure 8:
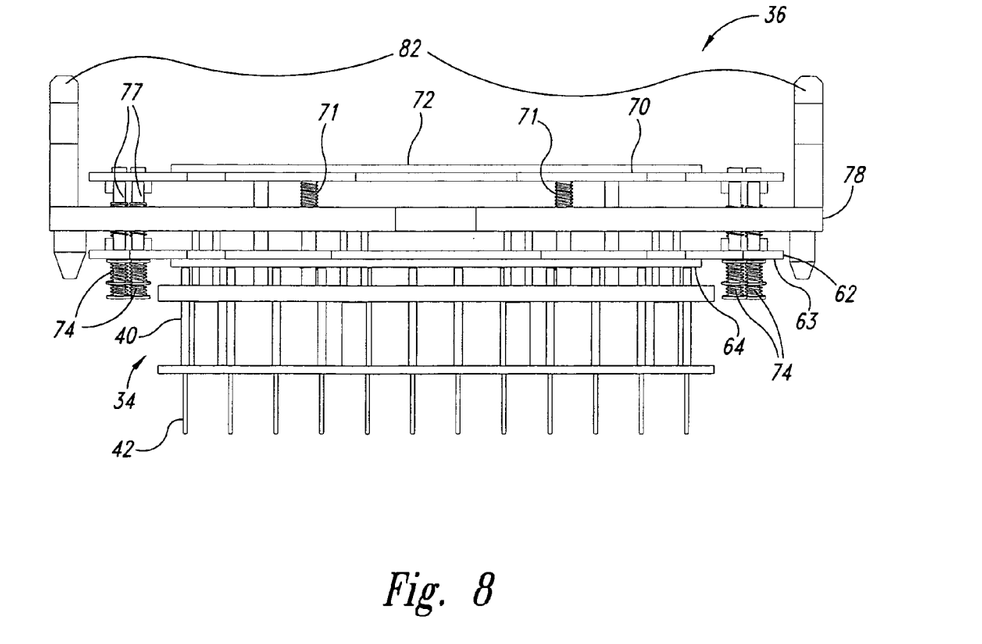
FIG. 8 is a front elevational view of the actuation assembly of FIG. 6 in a pin disengaged position.

As illustrated in FIGS. 4, 6, 7, 8 and 9, the actuation assembly 36 includes a pin engagement member 60 mounted for movement with respect to the pin support frame 32 between an engaged position contacting the ends 38 of the pins 34 and a disengaged position spaced from the engaged position. The engaged position is best illustrated in FIG. 8, and in broken line in FIG. 9. The disengaged position is best illustrated in FIG. 7, and in solid line in FIG. 9. The pin engagement member 60 may include a plate 62 having an engagement surface 63 and a resilient member or pad 64 attached to the engagement surface 63 of the plate 62.

Figure 9:
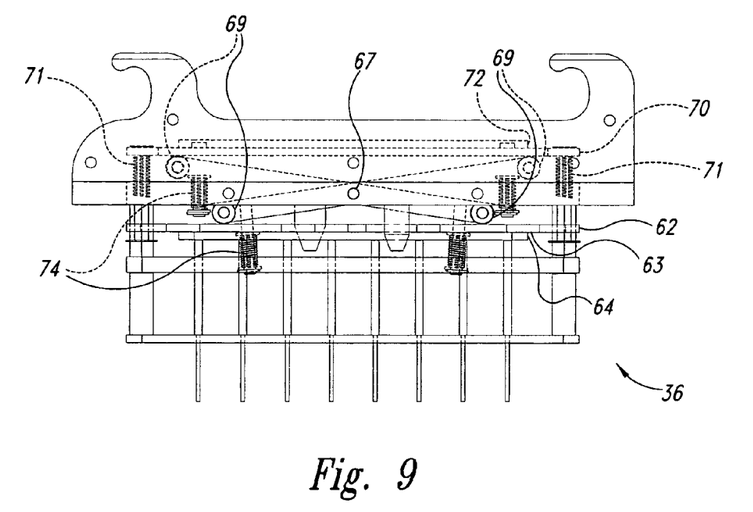
FIG. 9 is a right side elevational view of the actuation assembly of FIGS. 7 and 8 showing the pin engaged (broken line) and disengaged positions (solid line).

The actuation assembly 36 includes a linkage 66 coupled to move the pin engagement member 60 toward the disengaged position when a drive member such as the dispense head 26 of the dispensing apparatus 10 moves toward the pin support frame 32, and to move the pin engagement member 60 toward the engaged position when the drive member moves away from the pin support frame 32. The linkage 66 may, for example, take the form of a scissor linkage, as illustrated in FIGS. 4 and 9. The linkage 66 may include two pairs of linkage members, pivotally coupled by a pivot pin 67, to provide balance and even force across the pin engagement member 60. The linkage 66 may also includes rollers or bushings 69 at the extremities thereof.

The actuation assembly 36 may also include a pin engagement actuation member 68, opposed across the pin engagement member 60 from the pin support frame 36. The pin engagement actuation member 68 may include a plate 70 and resilient member or pad 72, the resilient pad 72 attached to a surface of the plate 70 which is engaged by the drive member, such as the dispense head 26. Thus, the linkage 66 couples the pin engagement actuation member 68 and the pin engagement member 60 to move the pin engagement member 60 toward the disengaged position as the pin engagement actuation member 68 moves toward the pin engagement member and the pin support frame 32, and to move the pin engagement member toward the engaged position as the pin engagement actuation member 68 moves away from the pin engagement member 60 and the pin support frame 32. The actuation assembly 36 may also include biasing members such as leaf springs or coil springs 71 to bias the pin engagement member 60 toward the disengaged position. The actuation assembly 36 may also include additional biasing members such as leaf springs or coil springs 74 biasing the arms of the linkage 66 into engagement with the plates 62, 70 in order to prevent unintended "chatter" or movement of the parts. Proper dimensioning of the various holes 75 and fasteners 77 received through the holes 75, also helps to reduce or eliminate chatter. (Only a small number of the fasteners 77 are illustrated for sake of clarity of the drawings.) As indicated in the Figures, many of the holes 75 may be countersunk, particularly where the holes 75 must accommodate springs 71.

Thus, the pin engagement member 60 engages the ends 38 of the pins 34 in a single plane in response to movement by a drive member such as the dispense head block 26, or a pin head block 76 illustrated in FIG. 10. With reference to FIG. 10, the pin head block 76 is similar to the dispense head block 26, however, the pin head block eliminates the internal cylinders 13 found in the dispense head block 26.

With continuing reference to FIGS. 4 and 6-9, the actuation assembly 36 may include an actuation assembly frame member 78 having a pair of slots 79 through which the linkage 66 is received and mounted via the pivot pins 67. The actuation assembly 36 also includes coupling members 80 which may have L-shaped ears or lugs 82 or other attachable/detachable coupling structures for selectively coupling the pin support assembly 30 to the carrier plate 16 (FIG. 1) of the fluid dispensing apparatus 10.

As best illustrated in FIGS. 3, 4 and 6, the pin support assembly 30 may include coupling members 80 for selectively engaging and disengaging the loading pins 24 of the movable carrier plate 16 (FIG. 1). The coupling members 80 may take the form of two pairs of generally L-shaped ears or lugs. The pin support assembly 30 may include a mating portion having a complementary shape to mate with the loading pins 24. For example the ears or lugs may include a lip formed at a distal end, defining an interior diameter sized and dimensioned to matingly receive a respective one of the loading pins 24.

Figure 11:
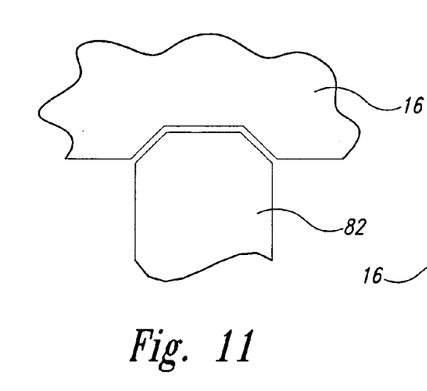
FIG. 11 is a partial, cross-sectional view along section 11 of FIG. 6, illustrating complementary mating portions of the coupling members on the pin support assembly and the carrier plate.
Figure 12:
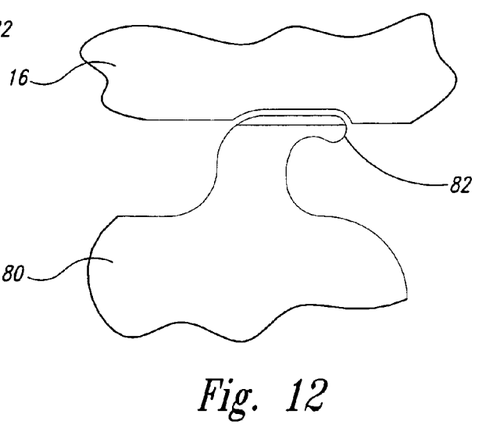
FIG. 12 is a partial, cross-sectional view along section line 12 of FIG. 6, further illustrating the complementary mating portions of the coupling members on the pin support assembly and the carrier plate.

The pin support assembly 30 may further include a mating portion having a complementary shape to mate with a mating potion of the dispense head apparatus 10. For example, as illustrated in FIGS. 11 and 12, the coupling members 80 may form all or a part of a mating portion for mating with a portion of the carrier plate 16. For instance, the coupling members 80 may, as illustrated, be tapered or curved in a first direction parallel to a direction of movement of the pin engagement actuation member 68 and may be tapered or curved in a second direction perpendicular to the direction of movement of the pin engagement actuation member 68. This ensures precise positioning of the pins 34 with respect to a target such as locations on a plate, slide or array.

Although specific embodiments of an examples for the dispensing apparatus are described herein for illustrative purposes, various equivalent modifications can be made without departing from the spirit and scope of the invention, as will be recognized by those skilled in the relevant art. The teachings provided herein of the invention can be applied to other dispensing apparatus, not necessarily the pin dispensing apparatus generally described above.

The various embodiments described above can be combined to provide further embodiments. All of the above U.S. patents, U.S. patent applications and publications referred to in this specification, including but not limited to U.S. application Ser. No. 10/214,943, filed Aug. 7, 2002, are incorporated herein by reference, in their entirety. Aspects of the invention can be modified, if necessary, to employ systems, circuits and concepts of the various patents, applications and publications to provide yet further embodiments of the invention. These and other changes can be made to the invention in light of the above detailed description. In general, in the following claims, the terms used should not be construed to limits the invention to the specific embodiments disclosed in the specification and the claims, which should be construed to include all dispensing apparatus that operate in accordance with the claims. Accordingly, the invention is not limited by the disclosure, but instead its scope is to be determined entirely by the following claims.

The invention claimed is:

1. An assembly operatively cooperatable with a piston plate of a dispense head apparatus to facilitate dispensing via a set of pins temporarily mounted with respect to the assembly, the assembly comprising:
   a pin engagement actuation member positionable to be selectively movably engaged by the piston plate of the dispense head;
   a pin engagement member opposed to the pin engagement actuation member and mounted for movement with respect thereto; and
   a linkage coupling the pin engagement actuation member and the pin engagement member to selectively move the pin engagement member away from the pin engagement actuation member as the pin engagement member moves towards an engaged position in which a portion of the pin engagement member contacts each pin in the set of pins to apply a force thereto, and to move the pin engagement member towards the pin engagement actuation member as the pin engagement member moves toward a disengaged position spaced from the engaged position in which the portion of the pin engagement member does not contact the pins in the set of pins.

2. The assembly of claim 1 wherein the assembly is selectively positionable to the dispense head apparatus in place of a box tray carrier of the dispense head apparatus.

3. The assembly of claim 1, further comprising:
   a set of lugs sized to receive a set of loading pins on the dispense head apparatus to selectively position the assembly with respect to the dispense head apparatus in place of a box tray carrier of the dispense head apparatus.

4. The assembly of claim 1, further comprising:
   a mating portion having a complementary shape to mate with a mating potion of the dispense head apparatus.

5. The assembly of claim 1, further comprising:
   a mating rail having a complementary shape to mate with a mating portion of the dispense head apparatus, the complementary shape of the mating rail being tapered in a first direction parallel to a direction of movement of the pin engagement actuation member and being tapered in a second direction perpendicular to the direction of movement of the pin engagement actuation member.

6. The assembly of claim 1 wherein the pin engagement member is a substantially flat pin engagement surface.

7. The assembly of claim 1 wherein the pin engagement member is a plate having a substantially flat pin engagement surface, and further comprising:
   a resilient pad attached to the pin engagement surface.

8. The assembly of claim 1 wherein the pin engagement actuation member is a plate having a piston plate engagement surface, and further comprising:
   a resilient pad attached to the piston plate engagement surface of the pin engagement actuation member.

9. The assembly of claim 1 wherein the pin engagement actuation member is engaged by the piston plate through one of a dispense head block and a pin head block.

10. An assembly operatively cooperatable with a piston plate of a dispense head apparatus to facilitate dispensing via a set of pins temporarily mounted with respect to the assembly, the assembly comprising:
   a pin engagement actuation member positionable with respect to the piston plate of the dispense head apparatus to be selectively movably engaged thereby;
   a pin engagement member opposed to the pin engagement actuation member and mounted for movement with respect thereto; and
   a scissors linkage coupling the pin engagement actuation member and the pin engagement member to selectively move the pin engagement member away from the pin engagement actuation member as the pin engagement member moves towards an engaged position in which a portion of the pin engagement member contacts each pin in the set of pins to apply a force thereto, and to move the pin engagement member towards the pin engagement actuation member as the pin engagement member moves toward a disengaged position spaced from the engaged position in which the portion of the pin engagement member does not contact the pins in the set of pins.

11. The assembly of claim 10, further comprising:
   a set of mounting members sized to receive a set of loading pins on the dispense head apparatus to selectively position the assembly with respect to the dispense head apparatus such that the pin engagement actuation member is movable by the piston plate of the dispense head apparatus.

12. The assembly of claim 10, further comprising:
a mating portion having a complementary shape to mate with a mating potion of the dispense head apparatus, the complementary shape of the mating portion being tapered in a first direction parallel to a direction of movement of the pin engagement actuation member and being tapered in a second direction perpendicular to the direction of movement of the pin engagement actuation member.

13. The assembly of claim 1 wherein the pin engagement member has a substantially flat pin engagement surface.

14. The assembly of claim 1 wherein the pin engagement member is a plate having a substantially flat pin engagement surface, and further comprising:
a resilient pad attached to the pin engagement surface.

15. The assembly of claim 1 wherein the pin engagement actuation member is a plate having a piston plate engagement surface, and further comprising:
a resilient pad attached to the piston plate engagement surface of the pin engagement actuation member.

16. A dispensing apparatus to facilitate dispensing via a set of pins temporarily mounted with respect to the dispensing apparatus, comprising:
a drive assembly frame; and
a drive member mounted to the drive assembly frame for axial movement with respect thereto;
a pin engagement actuation member positionable with respect to the drive assembly frame to be selectively movably engaged in response to the axial movement of the drive member;
a pin engagement member opposed to the pin engagement actuation member and mounted for movement with respect thereto; and
a linkage coupling the pin engagement actuation member and the pin engagement member to selectively move the pin engagement member away from the pin engagement actuation member as the pin engagement member moves towards an engaged position in which a portion of the pin engagement member contacts each pin in the set of pins to apply a force thereto, and to move the pin engagement member towards the pin engagement actuation member as the pin engagement member moves toward a disengaged position spaced from the engaged position in which the portion of the pin engagement member does not contact the pins in the set of pins.

17. The dispensing apparatus of claim 16 wherein drive assembly further comprises;
a head block movingly engagable by the drive member positioned to engage the pin engagement actuation member.

18. The dispensing apparatus of claim 16, further comprising:
a carrier plate having a set of loading pins to selectively attach and detach the carrier plate from the dispensing apparatus.

19. The dispensing apparatus of claim 16 wherein the linkage is a scissor linkage.

20. The dispensing apparatus of claim 16 wherein the linkage is a scissor linkage comprising at least two pairs of linkages arms, the linkage arms in each pair crossed and pivotally mounted with respect to one another.

* * * * *